US00PP22156P2

(12) United States Plant Patent
King et al.

(10) Patent No.: US PP22,156 P2
(45) Date of Patent: Sep. 20, 2011

(54) ***EUPHORBIA* PLANT NAMED 'GL MANAUS'**

(50) Latin Name: *Euphorbia hypericifolia*
Varietal Denomination: GL Manaus

(75) Inventors: Walt King, Clermont, FL (US); Jairo Schmidt, Sao Jose do Rio Preto (BR)

(73) Assignee: Athena Mudas, LTDA, Sao Jose Do Rio Preto SP (BR)

( * ) Notice: Subject to any disclaimer, the term of this patent is extended or adjusted under 35 U.S.C. 154(b) by 0 days.

(21) Appl. No.: 12/800,933

(22) Filed: May 26, 2010

(51) Int. Cl.
*A01H 5/00* (2006.01)

(52) U.S. Cl. ..... Plt./302

(58) Field of Classification Search ..... Plt./302
See application file for complete search history.

*Primary Examiner* — Annette Para

(74) *Attorney, Agent, or Firm* — Mark P. Bourgeois

(57) ABSTRACT

A new and distinct *Euphorbia* plant cultivar is disclosed, characterized by an upright, vigorous plant habit, bright green foliage, tall plant size and small, pure white flower bracts.

1 Drawing Sheet

Latin name of the genus and species: *Euphorbia hypericifolia.*

Variety denomination: 'GL MANAUS'.

BACKGROUND OF THE INVENTION

The new cultivar 'GL Manaus' is a product of a naturally occurring whole-plant mutation of an unnamed cultivar of *Euphorbia hypericifolia* (not patented). The new cultivar was discovered and selected as a single plant by Walt King and Jairo Schmidt in a controlled environment in a cultivated area of Manaus, Brazil in September of 2007.

Asexual reproduction of the new cultivar 'GL Manaus' by terminal cuttings was performed in São José do Rio Preto, Brazil and Oxnard, Calif., and has shown that the unique features of this new cultivar are stable and reproduced true to type on successive generations.

SUMMARY OF THE INVENTION

The cultivar 'GL Manaus' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GL Manaus.' These characteristics in combination distinguish 'GL Manaus' as a new and distinct *Euphorbia* cultivar:

1. An upright, vigorous plant habit;
2. Bright green foliage;
3. Tall plant size; and
4. Small, pure white flower bracts.

In comparison to the parent selection *Euphorbia hypericifolia*, 'GL Manaus' has a taller, more vigorous plant habit and has a consistently larger plant size than any *Euphorbia* plant on the market. Also, the foliage of 'GL Manaus' is a much brighter green than the parent selection. Finally, 'GL Manaus' has more pure white, cleaner flowers and is more uniform than the parent selection.

In comparison to the commercially available variety 'Inneuphdia' (U.S. Plant Pat. No. 17,567), the foliage of 'GL Manaus' is a much brighter green than the comparable variety. Also, 'GL Manaus' has a taller and more vigorous plant habit than the comparable variety. Finally, 'GL Manaus' has more pure white flowers than the comparable variety.

BRIEF DESCRIPTION OF THE PHOTOGRAPH

The accompanying photograph illustrates in full color a typical plant of 'GL Manaus' grown in a 1 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GL Manaus' plants grown in Oxnard, Ventura County, Calif., during the months of May through October. The growing temperature ranged from 12° C. to 15° C. at night to 12° C. to 20° C. during the day. Measurements and numerical values represent averages of typical flowering types.

Botanical classification: *Euphorbia hypericifolia* cultivar 'GL Manaus.'

Commercial classification: *Euphorbia.*

PROPAGATION

Type: By cuttings.

Time to initiate roots, summer: About 14 days at 20° C.

Time to initiate roots, winter: About 18 days at 20° C.

Time to develop roots: About 20 days at temperatures of 20.degree. C.

Root description: Fine, white in color.

Rooting habit: Freely branching.

PLANT

Growth habit: Tall and mounded plant habit; plants upright to outwardly spreading.

Height: Approximately 45 cm.

Plant spread: Approximately 54 cm.
Growth rate: Slow.
Branching characteristics:
Free Branching with four primary branches with secondary and tertiary lateral branches on each plant.
Lateral branch characteristics:
*Length.*—Approximately 38 cm.
*Diameter.*—Approximately 3 mm.
*Internode length.*—About 4 cm.
*Strength.*—Moderate.
*Texture.*—Smooth.
*Color.*—Near Green 138A.

FOLIAGE

Leaf:
*Arrangement.*—Opposite, simple.
*Average length.*—Approximately 3.2 cm.
*Average width.*—Approximately 1 cm.
*Shape of blade.*—Elliptic.
*Apex.*—Acuminate.
*Base.*—Rounded.
*Attachment.*—Stalked.
*Margin.*—Entire.
*Texture of top surface.*—Lightly pubescent.
*Texture of bottom surface.*—Lightly pubescent.
*Color.*—Young foliage upper side: Near Green 138A. Young foliage under side: Near Green 138B. Mature foliage upper side: Near Green 138A. Mature foliage under side: Near Green 138A.
*Venation.*—Type: Pinnate. Venation color upper side: Near Green 138B. Venation color under side: Near Green 138B.
Petiole:
*Average length.*—Approximately 1 cm.
*Color.*—Near Green 138A.
*Diameter.*—Less than 1 mm.

INFLORESCENCE

Inflorescence description:
*Natural flowering season.*—Spring to summer.
*Flowering habit.*—Continuous.
*Flower arrangement.*—Single rotate flowers arranged in umbel-like compound terminal cymes. Freely flowering with about 400 to 500 flower buds and flowers per plant, facing upright and outwardly.
*Persistence.*—Persistent.
*Fragrance.*—None detected.
*Inflorescence height.*—About 1.3 cm.
*Inflorescence diameter.*—About 1.4 cm.
*Flower diameter.*—About 7 mm.
*Flower depth.*—About 7 mm.
*Longevity.*—About 12 days.

Floral bracts:
*Quantity.*—Two.
*Arrangement.*—Opposite.
*Length.*—About 7 mm.
*Width.*—About 2 mm.
*Shape.*—Elliptical.
*Apex.*—Rounded.
*Base.*—Fused.
*Margin.*—Entire.
*Texture, upper and lower surfaces.*—Smooth.
*Color.*—When opening and fully expanded: Upper surface: Near White 155B. Lower surface: Near White 155B.
*Peduncles.*—Length: About 4 cm. Diameter: About 2 mm. Strength: Moderate. Angle: About 60 to 90 degrees from vertical. Texture: Smooth. Color: Near Green 138A.
*Pedicels.*—Length: About 4 mm. Diameter: About 1 mm. Strength: Moderate. Angle: About 45 degrees from vertical. Texture: Smooth. Color: Near Green 138A.
*Cyathia.*—Length: About 5 mm. Diameter: About 3 mm. Shape: Oval; eight terminal points. Aspect: Upright. Color: Near Green 138A.
*Nectaries.*—Quantity: About three or four per flower. Shape: Lunate. Length: About 2 mm. Width: About 2 mm. Color: Near Green 147B.

REPRODUCTIVE ORGANS

*Androecium.*—Quantity: About four stamens per cyathia. Shape: Oval, bi-lobed. Length: About 1 mm. Color: Near White 158B. Pollen: Scarce. Pollen color: Near 158D.
*Gynoecium.*—Quantity: One per cyathia. Pistil length: About 1 mm. Style length: Less than 1 mm. Style color: Near White 155B. Stigma shape: Six-parted. Stigma color: Near White 158D. Ovary color: Near Yellow-Green 147A.

OTHER CHARACTERISTICS

Disease resistance: Neither resistance nor susceptibility to diseases or pests has been observed in this variety.
Drought tolerance/cold tolerance: Plants of the new cultivar are tolerant to temperatures as low as 10° C. and as high as 40° C.
Fruit/seed production: Commercially, this plant is not used or observed in a stage where fruit or seeds would be produced. Therefore, seed or fruit production has not been observed.
What is claimed is:
1. A new and distinct cultivar of *Euphorbia* plant named 'GL Manaus' as herein illustrated and described.

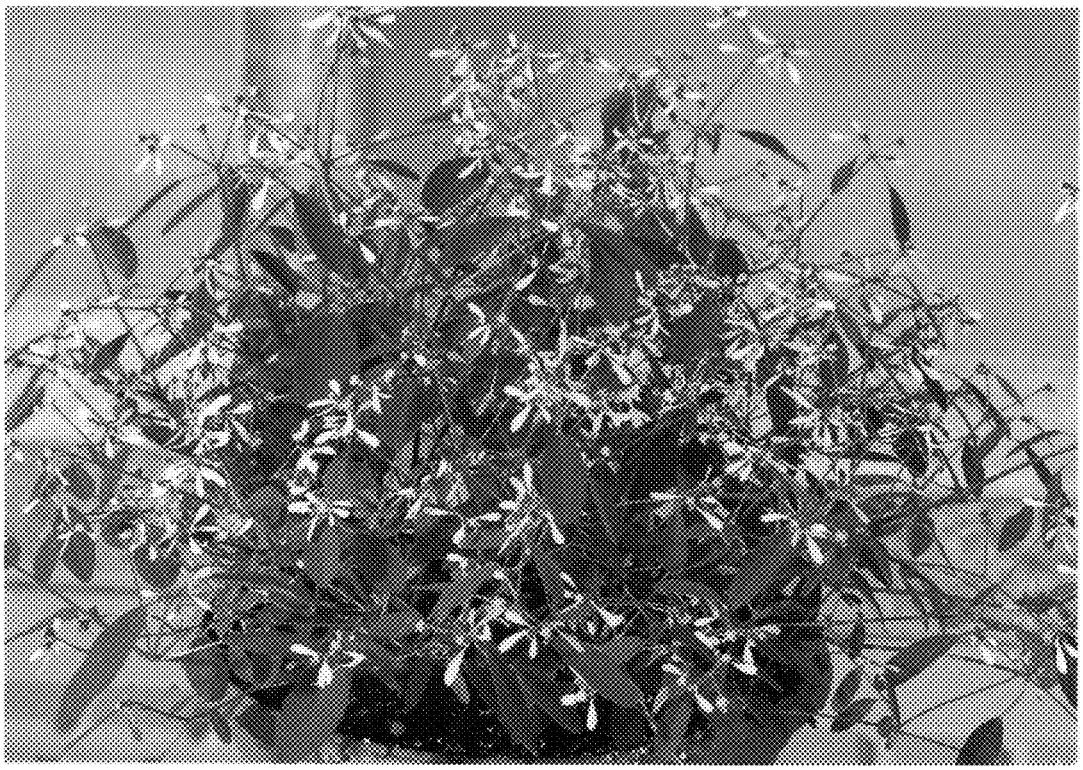

* * * * *